United States Patent
Schmidt et al.

(10) Patent No.: US 11,931,520 B2
(45) Date of Patent: Mar. 19, 2024

(54) DETERMINATION OF A TENDENCY OF A PASSENGER TO GET MOTION SICKNESS IN A VEHICLE

(71) Applicant: Ford Global Technologies, LLC, Dearborn, MI (US)

(72) Inventors: Eike Schmidt, Cologne (DE); Jelte Egbert Bos, Driebergen (NL); Stefan Wolter, Würselen (DE); Florian Golm, Herzogenrath (DE)

(73) Assignee: Ford Global Technologies, LLC, Dearborn, MI (US)

( * ) Notice: Subject to any disclaimer, the term of this patent is extended or adjusted under 35 U.S.C. 154(b) by 842 days.

(21) Appl. No.: 17/036,781

(22) Filed: Sep. 29, 2020

(65) Prior Publication Data

US 2021/0093827 A1 Apr. 1, 2021

(30) Foreign Application Priority Data

Sep. 30, 2019 (DE) .......................... 102019126396.4

(51) Int. Cl.
*A61M 21/02* (2006.01)
*B60K 35/00* (2006.01)
(Continued)

(52) U.S. Cl.
CPC .............. *A61M 21/02* (2013.01); *B60K 35/00* (2013.01); *G06F 3/011* (2013.01);
(Continued)

(58) Field of Classification Search
CPC . A61M 21/02; A61M 2021/005; B60K 35/00; B60K 2370/1529; B60K 2370/744; G06F 3/011
See application file for complete search history.

(56) References Cited

U.S. PATENT DOCUMENTS 9,994,228 B2  6/2018 Krueger
2006/0015000 A1*  1/2006 Kim ..................... A61M 21/02
                                                            600/27
(Continued)

FOREIGN PATENT DOCUMENTS

EP      2378948 A1   10/2011
JP      4882433 B2    2/2012
WO  2018070330 A1    4/2018

*Primary Examiner* — Thaddeus B Cox
*Assistant Examiner* — Joshua Daryl D Lannu
(74) *Attorney, Agent, or Firm* — Brandon Hicks; Eversheds Sutherland (US) LLP

(57) ABSTRACT

A method for detecting the tendency of a passenger of a vehicle to get motion sickness by using a rod and frame test is disclosed. An image designed to carry out a rod and frame test is displayed in the vehicle. The rod and the frame each enclose an angle greater than 0 degrees and less than 90 degrees with a horizontal spatial axis and/or a vertical spatial axis. A request is issued to correct the rod into a vertical or horizontal position by means of an input device. An input carried out by the passenger to correct the rod is recorded. The rod and frame test is evaluated by an evaluation device based on the recorded input of the passenger, and at least one measure is issued to prevent and/or combat the occurrence of motion sickness, depending on the result of the evaluation.

10 Claims, 2 Drawing Sheets

(51) Int. Cl.
    *G06F 3/01*    (2006.01)
    *A61M 21/00*   (2006.01)
(52) U.S. Cl.
    CPC ... *A61M 2021/005* (2013.01); *A61M 2230/63* (2013.01); *B60K 2370/1529* (2019.05); *B60K 2370/744* (2019.05)

(56) References Cited

U.S. PATENT DOCUMENTS

| | | | | |
|---|---|---|---|---|
| 2012/0121138 | A1* | 5/2012 | Fedorovskaya | G02B 27/017 |
| | | | | 382/107 |
| 2016/0228771 | A1* | 8/2016 | Watson | A63F 13/285 |
| 2018/0370461 | A1* | 12/2018 | Solar | A61M 21/00 |
| 2019/0269321 | A1* | 9/2019 | Murakami | G08G 1/16 |
| 2020/0238876 | A1* | 7/2020 | Dhaens | B60R 11/04 |
| 2020/0337623 | A1* | 10/2020 | Bulut | A61B 5/7275 |
| 2020/0353934 | A1* | 11/2020 | Vulcu | A61B 5/165 |

* cited by examiner

DETERMINATION OF A TENDENCY OF A PASSENGER TO GET MOTION SICKNESS IN A VEHICLE

CROSS-REFERENCE TO RELATED APPLICATIONS

The present disclosure claims priority to and the benefit of DE Patent Application No. 102019126396.4, filed Sep. 30, 2019, which is hereby incorporated by reference herein in it entirety.

FIELD

The present invention relates to a method for detecting a tendency of a passenger of a vehicle, in particular a motor vehicle, ship or aircraft, to get motion sickness by means of a rod and frame test in the interior of the vehicle. The invention relates to a device for carrying out this method, as well as a vehicle.

BACKGROUND

According to statistical studies, approximately 45% of vehicle passengers suffer from or are susceptible to motion sickness. On the other hand, drivers of vehicles are affected by motion sickness to a much lower extent, in particular because they control the vehicle themselves and thus have control over the movement of the vehicle and because they have a good view in the direction of travel. In connection with the introduction of autonomous driving, it is therefore to be feared that the incidence of motion sickness will increase, especially as former drivers are now becoming passengers and because in autonomous driving passengers will want to use the journey for other activities, for example for reading or working, especially on mobile devices. If motion sickness then occurs, this significantly worsens the comfort, and in particular the advantages of higher autonomy levels, such as SAE Level 3 or Level 4, could not be made accessible to a significant number of users in this case.

Studies show that there are large individual differences in susceptibility to get motion sickness, especially in terms of the triggering factors and the efficiency of certain countermeasures.

The Rod and Frame Test, RFT in brief, is a method for measuring "field-dependent" or "field-independent" cognitive styles (field dependence). In a darkened room, a rectangular frame with a rod in it appears on the wall, both hanging crookedly. The test subject sits on a chair, which is also inclined into the leaning plane—in relation to the floor—and also has its own footboard, so that the subject has no contact with the floor. The task is to bring the rod to the floor in a vertical position. Those who manage this relatively effortlessly are considered "field-independent". The decisive factor for this is proprioceptive perception, i.e. the orientation of impulses from the inside of the body.

Methods for measuring a person's spatial perceptual capacity are disclosed, for example, in documents EP 2 198 770 A1, U.S. Pat. No. 9,994,228 B2 and WO 2018/070330 A1.

SUMMARY

Against this background, it is the object of the present invention to provide an improved method for detecting and, where appropriate for combating the tendency of a passenger of a vehicle to get motion sickness, which in particular offers differentiated and individualized countermeasures. A further task is to provide a corresponding device and a correspondingly advantageous vehicle, in particular motor vehicle.

These objectives mentioned are achieved by a method for detecting the tendency of a passenger of a vehicle to get motion sickness according to Claim 1, a device for detecting the tendency of a passenger of a vehicle to get motion sickness according to Claim 7 and a vehicle according to Claim 10. The dependent claims contain further advantageous embodiments of the invention.

The method according to the invention for detecting and optionally for combating the tendency of a passenger of a vehicle to get motion sickness by means of a rod and frame test is designed to be carried out in the interior of a vehicle, for example a motor vehicle, ship or aircraft. The method includes the following steps: an image designed for performing a rod and frame test is shown on a display in the interior of the vehicle. The image includes at least one frame and a rod arranged in the frame, wherein the rod encloses an angle greater than 0° and less than 90° with a horizontal spatial axis and/or a vertical spatial axis. Subsequently, a request is issued, in particular to the passenger, to place or correct the rod in a vertical or horizontal position by means of an input device. An input of the passenger that is carried out to correct the rod is recorded. By means of an evaluation device, the rod and frame test is evaluated based on the recorded input of the passenger. Depending on the result of the evaluation, at least one measure is issued to combat or prevent the occurrence of motion sickness. In this process, the output is preferably carried out via an output device to the passenger, in particular in the form of a visual and/or acoustic output signal.

The method according to the invention has the advantage that the diagnosis and determination of a passenger's tendency to get motion sickness can be carried out within the vehicle. In addition, it is possible to output and offer personalized or individual measures adapted to the respective situation to prevent and/or combat motion sickness. This enables the possible occurrence of illness to be adapted to in a timely and individual manner and to be combated efficiently.

It has been scientifically proven that the psychological concept of field dependence correlates with the likelihood of the occurrence of motion sickness, especially the part triggered by a visual-vestibular conflict. This conflict is probably the main cause of motion sickness, for example when reading in a moving vehicle. By the method according to the invention which can be carried out in a vehicle, the passengers that tend to an appearance of motion sickness when reading in the moving vehicle can be individualized. This can be pointed out to them, which makes them aware of the tendency. Appropriate countermeasures may also be offered and taken if necessary.

Preferably, before carrying out the rod and frame test, the interior of the vehicle is darkened. This can be achieved, for example, by obscuring the window panes of the vehicle, for example by darkening windows or for example with blinds. In addition or alternatively, the vehicle can be brought into a dark environment, for example a garage. Darkening of the vehicle interior before or during the execution of the rod and frame test improves the test results, as the passenger is thus denied orientation to orientation points or objects located outside the vehicle.

In an advantageous variant, a screen permanently installed in the interior of the vehicle, for example, a display screen installed on or in a backrest of a vehicle seat and/or a head-up display and/or a virtual reality display device, for example a virtual reality helmet, is used as a display. The above display options have the advantage that display devices already present in the vehicle can also be used for carrying out the method according to the invention. In this respect, no additional equipment is required, and execution of the test in an efficient and cost-effective manner is therefore feasible.

A rotary knob and/or a steering wheel and/or a voice command input device and/or a touch screen can be used as an input device. Also these variants have the advantage that devices already present in the vehicle can be used for carrying out the method according to the invention.

In a further advantageous variant, the tendency of the passenger to get motion sickness is classified depending on the evaluation result. Depending on the classification, at least one measure may be taken to control or prevent the occurrence of motion sickness, in particular for the passenger concerned. The output can be carried out via a visually and/or acoustically perceptible output signal. The output can be carried out, for example, by means of a display, preferably the display which is also used to perform the test.

The evaluation result can be classified, for example by the categories "no susceptibility to get motion sickness" or "susceptibility to motion sickness", "no or low susceptibility to motion sickness" or "high susceptibility to motion sickness", or by the extent of field dependence in "field dependent" or "high susceptibility to motion sickness" and "field-independent" or "low susceptibility to motion sickness". In connection with the classification of the evaluation result, other characteristics of the passenger may also be taken into account, such as their age and/or gender and/or sensitivity to odors and/or temperature sensitivity and/or the ability to read in the vehicle without motion sickness. One or more of these properties can be entered into or recorded by the evaluation device.

As measures for the prevention and/or combating of motion sickness, which can be issued, for example, by means of the evaluation device, in particular as a control signal, for example, a recommendation to not read while in motion and/or displaying a horizontal line and/or displaying a camera image of the view in the direction of travel, i.e. ahead, and/or the supply of fresh air and/or the supply of cold air and/or the reduction of driving dynamics, come under consideration.

The recommendation to not read can be issued visually, for example by means of a display, or acoustically, for example by means of a loudspeaker. The horizontal line and/or the camera image of the view in the direction of travel can be displayed by means of a display which is present in the vehicle, for example a display arranged in a rear seat, or by means of a tablet or smartphone.

The device according to the invention for detecting the tendency of a passenger of a vehicle to get motion sickness by means of a rod and frame test comprises a display, at least one input device, an evaluation device, and an output device. Preferably, the display is also simultaneously the output device. The device according to the invention is designed to be arranged in a vehicle and operated in the vehicle according to a previously described method according to the invention. The display, the input device, the evaluation device, and the output device are connected to each other for signal and/or data transmission. The device according to the invention has the features and advantages already mentioned above.

In an advantageous variant, the display and/or the output device includes a screen permanently installed in the interior of the vehicle and/or a head-up display and/or a virtual reality display device, for example a VR helmet or VR glasses. The input device may include a rotary knob and/or a steering wheel and/or a voice command input device.

The vehicle according to the invention is designed to perform a method according to the invention described above. In addition or alternatively to this, the vehicle according to the invention comprises an already described device according to the invention. The vehicle is, for example, a motor vehicle, a ship, or an aircraft. The motor vehicle may be a passenger car, a truck, a bus, or a minibus. The vehicle may be designed for fully or partially autonomous driving. The vehicle according to the invention has the advantages already mentioned above.

BRIEF DESCRIPTION OF THE DRAWINGS

The invention is explained in more detail below on the basis of exemplary embodiments with reference to the attached figures. Although the invention is illustrated and described in detail by the preferred exemplary embodiments, the invention is not limited by the disclosed examples and other variations can be derived from this by the person skilled in the art without departing from the scope of protection of the invention.

The figures are not necessarily detailed and true to scale and may be enlarged or reduced to provide a better overview. Therefore, functional details which are disclosed here are not to be understood restrictively, but only as an illustrative basis, which provides guidance to the person skilled in this field of technology in order to use the present invention in a variety of ways.

The term "and/or" used here, if used in a series of two or more elements, means that each of the listed elements can be used alone, or any combination of two or more of the listed elements can be used. For example, if a composition is described as containing the components A, B and/or C, the composition A alone can be; B alone; C alone; A and B in combination; A and C in combination; B and C in combination; or A, B, and C in combination.

Figure 1:
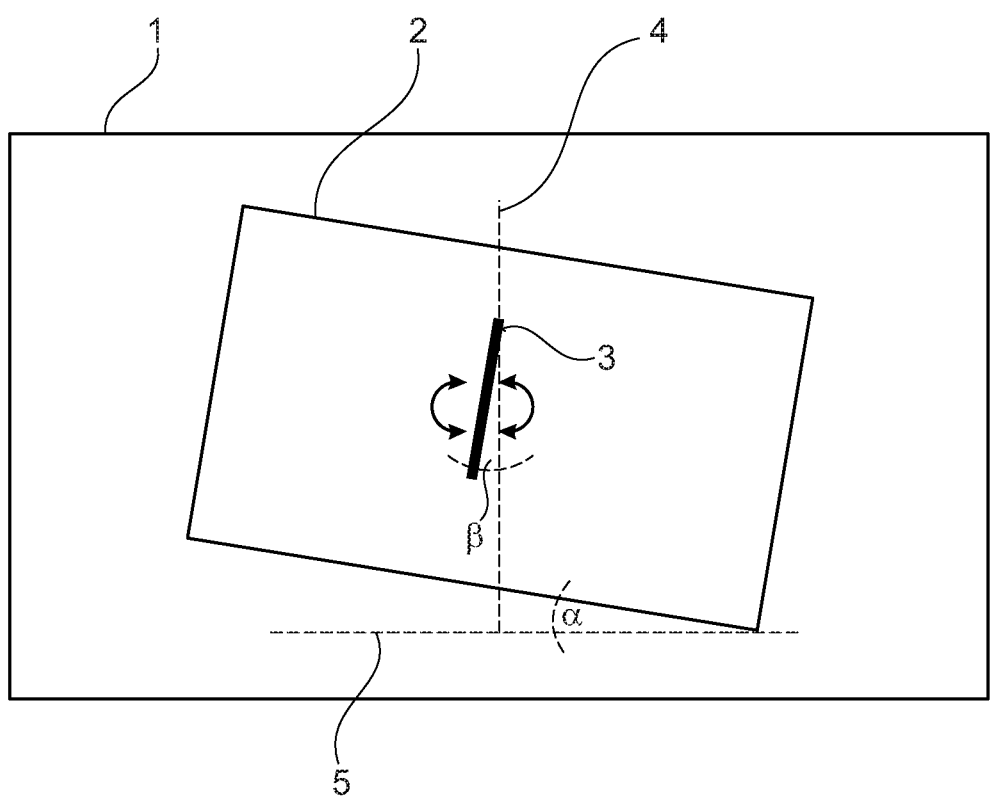

FIG. 1 shows schematically the principle of a rod and frame test.

Figure 2:
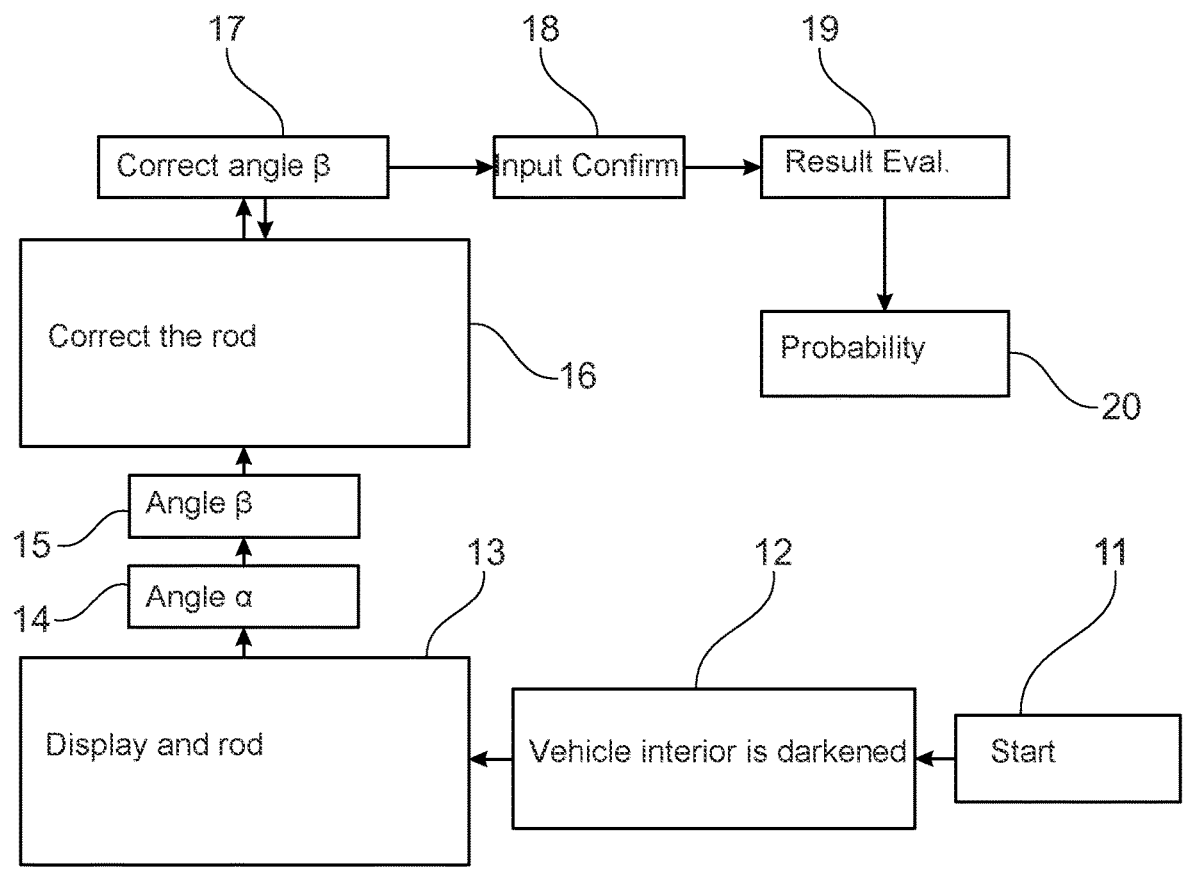

FIG. 2 shows schematically a flowchart for illustrating a method according to the invention.

Figure 3:
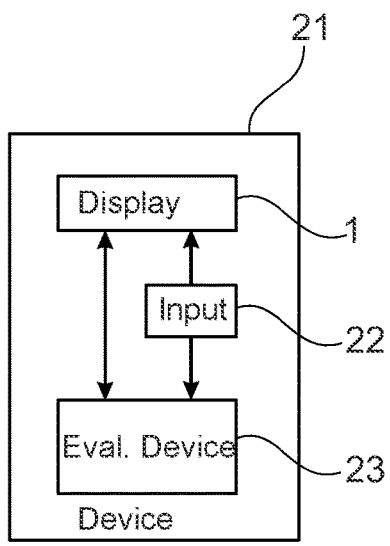

FIG. 3 shows schematically a device according to the invention.

Figure 4:
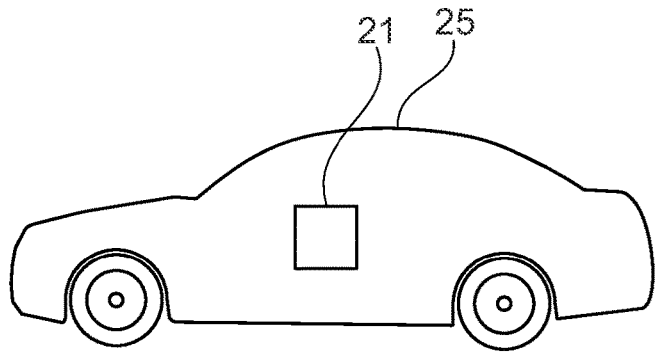

FIG. 4 shows schematically a vehicle according to the invention.

DETAILED DESCRIPTION

The principle of the rod and frame test is explained in more detail below on the basis of FIG. 1. FIG. 1 shows a display 1. A frame 2 and a rod 3 are displayed on the display 1. In this case, the frame 2 is tilted by an angle a with respect to a horizontal axis 5. In other words, an edge of the frame 2 encloses an angle α with an objective horizontal spatial axis 5. Rod 3 encloses an angle β with a vertical axis 4. The rod 3 may be shown tilted in particular with respect to the frame 2 and in relation to the vertical axis 4 and the horizontal axis 5. As part of the rod and frame test, the user is asked to correct the rod 3 into a vertical or horizontal position. The user is not shown the vertical axis 4 and the horizontal axis 5. The correction made by the user shows the extent to which the user is spatially oriented.

In FIG. 2, a schematic flowchart for a method according to the invention is shown schematically. The start of the method is indicated by reference number 11. In step 12, the vehicle interior is darkened, wherein this can be done by darkening window panes, with blinds or by positioning the vehicle in a dark or darkened environment, for example a garage. This is especially important, since it is known that any visual frame information, such as the contour or frame of a display, the position and orientation of the dashboard, etc. can distort the reliability of the rod and frame test. Therefore, a situation is preferably created in which only minimal or no light reaches the interior of the vehicle.

A tilted rectangular border is then displayed on a display 1, as shown in FIG. 1, for example. The display 1 can be a fixed display 1 in the vehicle, such as a centrally arranged display, a head-up display, a virtual reality display, or another display device. Preferably, a head-up display or a virtual reality display is used, in particular to avoid recognizable limiting frames of existing permanently installed displays. In the middle of the displayed frame 2, a randomly tilted rod 3 is displayed, as shown in particular in FIG. 1. The display of the frame 2 and the rod 2 on the display 1 is indicated with reference number 13. The tilting of the frame by an angle a is β is indicated by the reference number 15.

In step 16, the passenger is asked to place or correct the rod in a vertical position. This can be done, for example, by means of a rotary knob, a touch screen, a voice command input device, or a steering wheel. The correction of the angle β of the rod by the passenger is indicated by reference number 17. In step 1B, the input is confirmed by the passenger or user.

In step 19, the result is evaluated and in particular the level of field dependence is calculated. In step 20, the probability of the occurrence of motion sickness under certain conditions is determined. The result is output to the passenger by means of the display or via a voice message, for example. Preferably, individualized measures are issued for the prevention and/or avoidance of motion sickness.

The method may be carried out both on a front seat of a vehicle and on a rear seat. When carrying it out on the rear seat, in particular a display integrated in a backrest or a headrest can be used. For input by the user, a portable device, for example mobile phones, smartphones, or devices for voice recognition can be used, each of which is coupled to the display and an evaluation device for data transmission. The method can be repeated several times. In particular, this can improve the reliability of the measurement result and the individualization. Furthermore, training and habituation effects can be recorded.

FIG. 3 shows an example of a device according to the invention. The device 21 according to the invention for detecting the tendency of a passenger of a vehicle to get motion sickness by means of a rod and frame test comprises a display 1, at least one input device 22, an evaluation device 23 and an output device, which is preferably the display 1. The device 21 according to the invention is designed to perform a method described in connection with FIGS. 1 and 2. The display 1, the input device 22 and the evaluation device 23 are connected to each other for signal and/or data transmission. This is indicated by arrows.

FIG. 4 shows schematically a motor vehicle 25 according to the invention. The motor vehicle comprises a previously described device 21 according to the invention.

The invention claimed is:

1. A method for detecting a tendency of a passenger of a vehicle (25) to get motion sickness using a rod and frame test, the method comprising:

displaying, on a display (1) in an interior of the vehicle (25), an image designed to carry out the rod and frame test, which comprises at least one frame (2) and a rod (3) arranged in the frame (2), wherein the rod (3) and the frame (2) each enclose an angle ($\alpha$, $\beta$) greater than 0 degrees and less than 90 degrees with a horizontal spatial axis (5) and/or a vertical spatial axis (4), issuing a request to correct the rod (3) into a vertical or horizontal position by an input device (22), recording an input carried out by the passenger (18) for the correction of the rod (3), evaluating the rod and frame test by an evaluation device (23) based on the input of the passenger, and outputting, based on evaluating the rod and frame test, at least one measure to prevent and/or combat the occurrence of motion sickness.

2. The method according to claim 1, wherein before carrying out the rod and frame test, the interior of the vehicle (25) is darkened.

3. The method according to claim 2, wherein the interior of the vehicle (25) is darkened by darkening the vehicle's window panes and/or by bringing the vehicle into a dark environment.

4. The method according to claim 1, wherein a display screen permanently installed in the interior of the vehicle (25) and/or a head-up display and/or a virtual reality display device (VR helmet) is used as the display (1).

5. The method according to claim 1, wherein a rotary knob and/ or a steering wheel and/or a voice command input device and/or a touch screen is used as the input device (22).

6. The method according to claim 1, wherein depending on the result of the evaluation, the passenger's tendency to motion sickness is classified and, depending on the classification, at least one measure is output to prevent and/or combat the occurrence of motion sickness.

7. A device (21) for detecting a tendency of a passenger of a vehicle (25) to get motion sickness using a rod and frame test, the device comprising:

a display (1), at least one input device (22), an evaluation device (23) and an output device (1)

wherein the device is configured to be arranged in the vehicle (25) and operated in the vehicle (25) according to the method of claim 1.

8. The device (21) according to claim 7, wherein the display (1) includes a screen which is permanently installed in the interior of the vehicle (25) and/or a head-up display and/or a virtual reality display device.

9. The device (21) according to claim 7, wherein the at least one input device (22) includes a rotary knob and/or a steering wheel and/or a voice command input device.

10. A method, comprising:

displaying, on a display (1) in an interior of a vehicle (25), an image associated with a rod and frame test, wherein the image comprises a frame (2) and a rod (3) arranged in the frame (2), wherein the rod (3) and the frame (2) each enclose an angle ($\alpha$, $\beta$) greater than 0 degrees and less than 90 degrees with a horizontal spatial axis (5) and/or a vertical spatial axis (4), requesting a user correct the rod (3) into a vertical or horizontal position by an input device (22), recording an input by the user to correct the rod (3), evaluating the rod and frame test based on the input of the user, and outputting, depending on a result of the evaluation, at least one measure to prevent and/or combat an occurrence of motion sickness.

\* \* \* \* \*